United States Patent [19]

Sindo et al.

[11] 4,374,827

[45] Feb. 22, 1983

[54] WATER SOLUBLE EXTRACT FROM NONPATHOGENIC AEROBIC CORYNEBACTERIA

[75] Inventors: Tiuzi Sindo; Tadashi Obara, both of Tokyo; Hidenari Adachi, Osaka, all of Japan

[73] Assignee: Yamanouchi Pharmaceutical Co., Ltd., Tokyo, Japan

[21] Appl. No.: 267,768

[22] Filed: May 28, 1981

Related U.S. Application Data

[63] Continuation-in-part of Ser. No. 179,798, Aug. 20, 1980, abandoned.

[30] Foreign Application Priority Data

Aug. 30, 1979 [JP] Japan ................................ 54-110724

[51] Int. Cl.³ ..................... A61K 39/02; A61K 35/78; A61K 37/00
[52] U.S. Cl. ...................................... 424/92; 424/195; 424/177
[58] Field of Search ......................... 424/195, 92, 177

[56] References Cited

U.S. PATENT DOCUMENTS

4,013,788  3/1977  Jolles et al. ......................... 424/195
4,201,768  5/1980  Ciorbaru nee Sfartz et al. ... 424/195

OTHER PUBLICATIONS

Sindo et al., "Int. Archs Allergy Appl. Immun.", 59: 447-451, (1979).

*Primary Examiner*—Donald B. Moyer
*Attorney, Agent, or Firm*—Burgess, Ryan and Wayne

[57] ABSTRACT

A water soluble extract from nonpathogenic aerobic corynebacteria such as Corynebacterium equi Ko-85 strain, the said water soluble extract having the following characteristics:
  (a) protein content: 3.9–5.5 mg/ml (on the basis of Bovine Serum Albumin),
  (b) sugar component: 0.41–0.52 mg/ml (on the basis of glucose),
  (c) nucleic acid like substance: optical density in 260 nm/280 nm (ratio) of 1.56–1.62, and
  (d) isoelectric point: 3.75–3.80.

The extract possesses an anti-allergic effect, an anti-cancer effect, and an immunopotentiative effect and is particularly useful as an anti-allergic agent.

4 Claims, 5 Drawing Figures

WATER SOLUBLE EXTRACT FROM NONPATHOGENIC AEROBIC CORYNEBACTERIA

CROSS-REFERENCE TO RELATED APPLICATION

This application is a Continuation-In-Part of co-pending application Ser. No. 179,798, filed Aug. 20, 1980, now abandoned.

BACKGROUND OF THE INVENTION

1. Field of the Invention

This invention relates to a novel water soluble extract from nonpathogenic aerobic corynebacteria. More particularly, the invention relates to a water soluble extract from nonpathogenic aerobic bacteria, the said extract having the following characteristics:

(a) protein content: 3.9–5.5 mg/ml (on the basis of Bovine Serum Albumin (BSA)), (b) sugar component: 0.41–0.52 mg/ml (on the basis of glucose), (c) nucleic acid like substance: optical density in 260 nm/280 nm (ratio) of 1.56–162, and (d) isoelectric point: 3.75–3.80 as well as a process of producing the extract and pharmaceutical compositions containing the extract.

2. Description of the Prior Art

It has recently been reported in various literature that cultured broth (bacterial cells) of anaerobic corynebacteria cells such as of Corynebacterium parvum and the extracts from such corynebacterial cells have ananticancer effect and a protective effect against infection but there had been no reports on cultured broths of aerobic corynebacteria cells. The inventors previously found that cultured broth (bacterial cells) obtained by cultivating bacterial strains belonging to nonpathogenic aerobic corynebacteria had not only an anti-cancer effect and an immunopotentiating effect for spleen cells and lymphocytes but also an anti-allergic effect which had never been attributed to a cultured broth of anaerobic corynebacteria (see, Japanese Pat. Publn. (OPI) No. 47,909/'77). However, the formerly described cultured broth (bacterial cells) were practically unsuitable for use as medicaments due to the following reasons. Since the cultured broth (bacterial cells) was insoluble in water, it must be administered in the form of a suspension. When this suspension is administered subcutaneously, it causes a marked induration at the site of injection; this is known in the case of subcutaneous injection of BCG. This adverse skin reaction makes it intolerable to continue multiple administration. As well as these practical difficulties, the cultured broth (bacterial cells) show strong toxicity.

SUMMARY OF THE INVENTION

As the result of further investigations, the inventors have now succeeded in extracting water soluble active materials from the cultured broth (bacterial cells) of nonpathogenic aerobic corynebacteria having various useful pharmacological properties which can be practically used as medicaments.

That is, the invention provides a water soluble extract from nonpathogenic aerobic corynebacteria, the said extract having the following characteristics:

(a) protein content: 3.9–5.5 mg/ml (on the basis of Bovine Serum Albumin), (b) sugar component: 0.41–0.52 mg/ml (on the basis of glucose), (c) nucleic acid like substance: optical density in 260 nm/280 nm (ratio) of 1.56–1.62, and (d) isoelectric point: 3.75–3.80.

The water soluble extract of this invention has an anti-cancer effect, an immunopotentiative effect and a particularly strong anti-allergic effect and is also characterized by low toxicity as compared with the primarily cultured broth (bacterial cells). Furthermore, since the active materials of this invention are soluble in water, they can be administered by subcutaneous or intradermal injection for multiple dosing without causing induration of the skin and hence they can be used analogously for a desensitization therapy which is an important therapy for allergic diseases. Thus, the water soluble extract of this invention can be practically used as a medicament. Although the details of the structural compositions of the water soluble extract of this invention are not clear, it has been confirmed that the extract is a glycoprotein substance containing proteins, sugar, and nucleic acid like substances at definite ratios.

The ratio of the protein content against one part of the sugar component which is calculated from the content test results on protein and sugar (see the table in Production Example 1) is 3.9/0.52–5.5/0.41, i.e., 7.50/13.42 parts.

Accordingly- as long as the ratio is not changed, it is clear that use of the extract in its diluted state is naturally included in the range of this invention.

DESCRIPTION OF THE PREFERRED EMBODIMENT

Figure 1A:
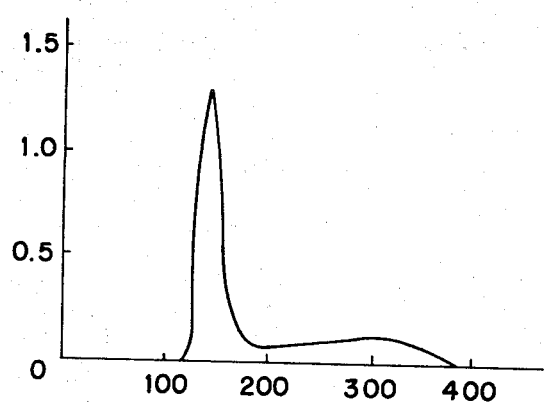
FIG. 1a is a graph showing the elution pattern of the extract of this invention in Sephadex G-200 Gel.

As the bacterial strains used in this invention belonging to the nonpathogenic aerobic corynebacteria, there are Corynebacterium equi Ko-85 strain, Corynebacterium pyogenes Tojo Hai strain, Corynebacterium xerosis 53-K-1 strain, and Corynebacterium renale Utsunomiya-Ushi strain. These strains are easily available to persons skilled in the art and are also preserved in the Medical Research Institute of Tokyo University as standard strains. The particularly preferred bacterial strain used in this invention is Corynebacterium equi Ko-85 strain. The cultured broths (bacterial cells) of these nonpathogenic aerobic corynebacteria can be obtained by aerobic culture of the corynebacteria according to a method usually used for the aerobic cultivation of corynebacteria cells as described in the Reference example shown below.

The water soluble extract of this invention is obtained by subjecting the primarily cultured broths thus obtained, that is, the cultured broth (bacterial cells) obtained by aerobic culture of bacterial strains belonging to nonpathogenic aerobic corynebacteria at a low-temperature treatment involving grinding and homogenizing the cultured broth (bacterial cells), subjecting the homogenates obtained to an ultrasonic treatment to separate the effective components, adjusting the pH of an aqueous solution of the effective components to 3.7–3.75 to form precipitates, forming an almost neutral aqueous solution of the precipitates and dialyzing the aqueous solution. The extract obtained is converted into a powdery solid product by lyophilizing it using a conventional method. In addition, the above-described methods for obtaining the extract are practiced according to conventional methods.

The water soluble extract of this invention has an anti-allergic effect, an anti-cancer effect, and an anti-allergic agent. And it is clear by the experimental results shown below that a water soluble extract of this invention possess excellent pharmacological action and weak toxicity.

The invention also relates to pharmaceutical compositions containing the water soluble extracts described above in combination with one or more diluents or excipients which are compatible and pharmaceutically acceptable. The pharmaceutical compositions of this invention may be administered by the oral, rectal or parenteral route or in aerosols. In human therapy, the dosages are a function of the desired effect. The dosages may be 10 ng to 500 µg per day for an adult patient.

The invention will be then further described by the following non-limiting examples.

Reference example (Production of primarily cultured broth (bacterial cells)):

*Corynebacterium equi* Ko-85 strain was cultivated at 37° C. for 5 days using a culture medium prepared by adjusting the pH of a mixture of 10 g of a meat extract, 10 g of peptone, 10 g of glucose, 1 g of sodium chloride, and 1000 ml of redistilled water to 7.4 with an aqueous sodium hydroxide solution. Then, after continuous centrifugation at a current speed of 50 ml/min. and at 10,000 r. p. m., the precipitates (bacterial cells) formed were washed centrifugally three times with an isotonic sodium chloride solution to provide a primary cultured broth (bacterial cells).

The yield of the cultured broth (bacterial cells) obtained was 17.0 g (wet weight) per 10 liters of the cultured medium used.

In addition, the relation between the yield of the cultured broth and the cultured period of time in the reference example by a turbidimetric determination is as shown in the following table; the maximum yield is obtained about 120 hours after the cultivation.

| Cultured time (hour) | O.D.* of Corynebacterium equi Ko-85 |
| --- | --- |
| 0 | 0.175 |
| 4 | 0.165 |
| 20 | 0.320 |
| 30 | 0.400 |
| 50 | 0.720 |
| 70 | 0.770 |
| 120 | 1.075 |
| 1 week | 1.070 |

*optical density

PRODUCTION EXAMPLE 1

After sufficiently washing 50 g of the primary cultured broth (bacterial cells) with an isotonic sodium chloride solution, the cultured broth was subjected to a low-temperature treatment for longer than 48 hours at −20° C. and the bacterial cells were pulverized by means of a Vibrogen cell mil (VCH-1). The homogenate formed was suspended in a suitable amount of water or a diluted aqueous sodium hydroxide solution and after an ultrasonic treatment of 20 KC 6 times each for 10 minutes in ice water, the suspension was extracted under shaking. Thereafter, 150 g of the extract obtained was centrifuged for 60 minutes at 105,000 g to remove bacterial cell residues and insoluble materials.

The supernatant formed was adjusted to a concentration corresponding to 25% wet bacterial cells and after adjusting correctly the pH thereof to 3.7–3.75 using 1 N hydrochloric acid at 8°–10° C., the precipitates were incubated over 48 hours. The precipitates were collected by centrifuging, dissolved in water at pH 7.2, the solution was dialyzed overnight, and after adjusting the pH of the system to 7.0, the system was subjected to centrifugal separation for 60 minutes at 12,000 g to form a supernatant (extract), which was lyophilized. The yield of the product was 500 mg (dry weight).

The physicochemical characteristics of the product were as follows:

A. Properties

The appearance of the extract was a light yellow-brown transparent liquid.

When the pH of the extract was adjusted to 3.75–3.80, precipitates formed.

B. Content

Three test samples (extracts) were separately prepared by the manner described above, which are shown by No. 1, No. 2, and No. 3, respectively. The contents of these test samples are shown in the following table.

|  | No. 1 | No. 2 | No. 3 |
| --- | --- | --- | --- |
| Protein content*[1] (mg/ml) | 4.3 | 3.9 | 5.5 |
| Sugar component*[2] (mg/ml) | 0.46 | 0.41 | 0.52 |
| Nucleic acid like substance*[3] (OD 280 nm) | 1.13 | 0.90 | 1.10 |
| Nucleic acid like substance*[3] (OD 260 nm) | 1.83 | 1.42 | 1.72 |
| Nucleic acid like substance*[3] (260 nm/280 nm) | 1.62 | 1.58 | 1.56 |
| Isoelectric point (pH) | 3.75 | 3.75 | 3.80 |

*[1]Protein content (Copper-Folin method)
*[2]Sugar component (phenol sulfuric acid method)
*[3]Nucleic acid like substance The extract was diluted with water to 10 times the volume of the extract and after adding 3 ml of solution C shown between to 0.6 ml of the dilution, it was reacted for 10 minutes. After the reaction was over, 0.3 ml of a phenol solution (prepared by diluting a commercially available product with water) was added to the reaction mixture and after allowing the mixture to stand for 30 minutes at room temperature, the optical density (O.D.) at 500 nm was measured. A standard curve by BSA was made in a concentration range of 0.2–1.0 mg/ml and from the standard curve, the content in the extract was determined.

Solution A: To a 0.1 N sodium hydroxide solution was added sodium carbonate at a concentration of 2%.

Solution B: To a 10% sodium citrate solution was added copper sulfate at a concentration of 0.5%.

Solution C: A mixture of 50 ml of solution A and 1 ml of solution B (50:1).

The extract was diluted with water to 10 times the volume of the extract and then 1 ml of a 5% phenol solution and 5 ml of sulfuric acid were immediately added to 1 ml of the dilution. After allowing the mixture to stand for 20 minutes, the optical density (O.D.) at 490 nm was measured. A standard curve with an aqueous glucose solution was made in a concentration range of 0.02–0.2 mg/ml and from the standard curve, the content in the extract was determined.

The extract was diluted with water to 20 times the volume of the extract, the optical densities (O.D.) at 260 nm and 280 nm were measured, and their ratio was determined.

The elution pattern of the extract of this invention in Sephadex G-200 gel shows a single peak as shown in FIG. 1a.

The bed volume was 3.0×60 cm², the elution buffer was a 0.01 M phosphate buffer, and the flow rate was 20.8 ml/hour. The ordinate axis shows an optical density at 280 nm and the abscissa axis shows an elution volume (ml).

Figure 1B:
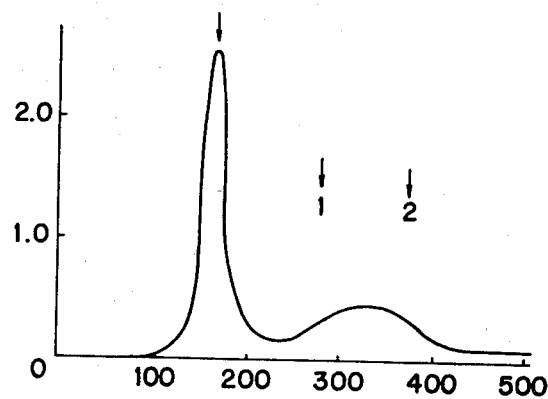
FIG. 1b is a graph showing the elution pattern of the extract of this invention in ultrogel ACA 34.

Also, the elution pattern of the extract of this invention in Ultrogel ACA 34 is shown in FIG. 1b.

The column size was 2.8×84 cm², the elution buffer was a 0.01 M phosphate buffer (containing 0.85% sodium chloride), and the flow rate was 14.0 ml/hour. The ordinate axis shows an optical density at 280 nm, the abscissa axis shows an elution volumn (ml), the arrow 1 shows the position of bovineγ-globulin (molecular weight: 160,000) and the arrow 2 shows the position of soybean trypsin inhibitor (molecular weight: 21,700).

PRODUCTION EXAMPLE 2

After subjecting 152 g of the primary cultured broth (bacterial cells) to a low-temperature treatment for 48 hours at −20° C., the cultured broth (bacterial cells) was suspended in distilled water together with glass beads of 0.1 mm diameter and the suspension was treated 10 times by a Vibrogen cell mill (VCH-1) at 4500 r.p.m. for 30 minutes at 0° C. to grind and homogenize the bacterial cells. Then, after centrifugation, the supernatant formed for 10 minutes at 1,000 r.p.m., the supernatant was subjected to an ultrasonic treatment at 20 KC for 15 minutes in ice water, then centrifuged for 20 minutes at 3000 r.p.m. and then for 40 minutes at 16,000 r.p.m. (20,000 g) to remove bacterial cells residues and insoluble materials. The supernatant was adjusted to a concentration corresponding to 25% wet bacterial cells, the pH thereof was correctly adjusted to 3.70 using a 1 N hydrochloric acid at 4° C. and allowed to stand overnight to complete the precipitation. The precipitates were collected by centrifugation for 30 minutes at 5,000 r.p.m., dissolved in distilled water after adjusting the pH thereof to 7.0 with 1 N sodium hydroxide, the solution was dialyzed overnight with distilled water at 4° C. and then for 2 days with an isotonic sodium chloride solution at the same temperature. The pH was adjusted to 7.0 followed by centrifugation for 40 minutes at 16,000 r.p.m. (20,000 g), the supernatant was filtered by means of a membrane filter (Millipore HA) to provide about 500 ml of an extract, which was then lyophilized.

The results of the pharmacological test and the toxicity test on the extracts of this invention are shown below:

A. Suppressive effect on immunoglobulin E (IgE) antibody:

In an isotonic sodium chloride solution was suspended 2 μg of DNP-OA together with an aluminum hydroxide gel and after administering the suspension to BALB/c mice by intraperitoneal injection, 600 μg of the extract of this invention was administered on 2 and 7 days after immunization. Sera were collected from animals on day 5, 10, 15, 20, 25 and 30 after immunization and the pooled sera were used for sensitization of the skins of the hind back portions of SD rats. After 4 hours, a solution of antigen, DNP-BSA containing 0.5% Evans blue was injected into the tail veins, and the IgE titer was measured by the amount of the dye extracted from reaction site. The results are shown in FIG. 2.

Figure 2:
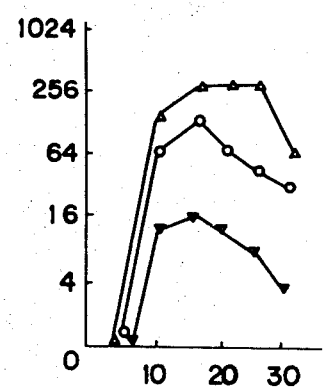
FIG. 2 is a graph showing the suppressive effects on reaginic antibody production of the extract of this invention.

FIG. 2 shows the suppressive effect on the reaginic antibody production by the extracts of this invention.

DNP-OA sensitized BALB/c mice were grouped into three groups, group 1 mice ▼-▼were inoculated with the extract of this invention, group 2 mice ▲—▲ with killed bacterial cells of aerobic *Corynebacterium parvum*, and group 3 mice ○—○with in a physiological sodium chloride solution on 2 and 7 days after the sensitization, and the effect of treatment on IgE antibody production was examined.

The ordinate axis shows the IgE antibody titer and the abscissa axis shows days after the DNP-OA sensitization.

From the results shown in FIG. 2, it is clear that the extract of this invention suppresses the IgE antibody production which triggers an immediate type of allergy.

B. Suppressive effect on passive cutaneous anaphylaxises (PCA) by local treatment:

The skins of SD rats were first treated with the extract of this invention. Two hours later, the rats were inoculated with anti-DNP (hapten) IgE antibody at the same area of the skins, and passive cutaneous anaphylaxises (PCA) were done to detect the suppressive effect of the extract of this invention. The results are shown in Table I.

TABLE I

| Extract of the invention (mg) | Amount of Dye extracted (μg) Dilution of antibody solution | | | | | |
|---|---|---|---|---|---|---|
| | ⅛ | 1/16 | 1/32 | 1/64 | 1/128 | 1/256 |
| 5.0 | 11.2 | 12.0 | 11.8 | 9.4 | 7.5 | — |
| | (29) | (19) | (19) | (17) | (10) | |
| | 11.3 | 10.7 | 12.7 | — | — | — |
| | (28) | (28) | (13) | (100) | | |
| 2.5 | 13.1 | 12.6 | 11.5 | 7.7 | — | — |
| | (17) | (15) | (21) | (32) | | |
| | 12.1 | 12.8 | 11.6 | 7.2 | — | — |
| | (23) | (14) | (21) | (36) | | |
| 1.0 | 16.8 | 14.6 | 15.0 | 10.0 | 6.5 | trace |
| | (0) | (2) | (0) | (12) | (22) | |
| | 15.2 | 15.4 | 14.8 | 10.1 | — | — |
| | (3) | (0) | (0) | (11) | | |
| physiological sodium chloride soln. | 15.7 | 14.9 | 14.6 | 11.3 | 8.3 | trace |

(Note)
In the above table, the numerals in the parentheses show the suppressive rates on PCA reaction.

As shown in the table, the extract of this invention blocks binding of IgE antibody on target cells (mast cells, basophils, etc.,) and suppresses the liberation of histamine at antigen invasion.

C. Suppressive effect on passive cutaneous anaphylaxises (PCA) by systemic treatment.

The PCA suppressive effect was more remarkable in the case of treating with the extract of this invention before the IgE antibody sensitization than the case of treating after the sensitization. The results are shown in the following table, in which the amount of extract of this invention used for the treatment was 1.0 mg and the PCA value was shown by the amount of dye extracted.

TABLE I-B

| Treated time of extract of the invention (time before or after antibody sensitization) | Amount of dye extracted ($\mu$g) Dilution of antibody solution | | |
|---|---|---|---|
| | 1/20 | 1/40 | 1/80 |
| −24 | 27.3 ± 8.1 (60) | 16.0 ± 6.5 (54) | 6.5 ± 4.3 (47) |
| −8 | 14.3 ± 4.8 (32) | 8.3 ± 3.8 (28) | 2.4 ± 1.1 (17) |
| −2 | 20.7 ± 8.8 (46) | 12.3 ± 6.9 (42) | 5.0 ± 3.1 (36) |
| 0 | 32.0 ± 11.3 (71) | 21.5 ± 11.5 (73) | 12.0 ± 8.5 (87) |
| +2 | 43.1 ± 8.1 (95) | 29.4 ± 13.1 (100) | 11.9 ± 7.9 (86) |
| +4 | 40.9 ± 10.0 (90) | 28.6 ± 11.9 (97) | 10.0 ± 6.4 (72) |
| Control | 45.3 ± 12.9 | 29.4 ± 10.8 | 13.8 ± 8.3 |

(Note)
The numerals in the parentheses show the ratios compared with the control.

The above-described experimental results show that the extract of this invention inhibits passive cutaneous anaphylaxises elicited by mast cells or basophils by binding of IgE antibody, which was sensitized with antigen, regardless of the kind of antigen and also suppresses allergic reaction in a wide range thereafter.

D. Increasing effect for producing antihapten IgG, (IgM) antibody:

The extract of this invention was intravenously injected into 7 week old BALB/c mice in an amount of 0.1 mg and then the mice were intravenously sensitized with 100 $\mu$g of DNP-OA on 7 and 14 days after the immunization. Three days later, the number of antibody forming cells in the spleen cells was measured by Cunningham's indirect method using DNP-BSA sensitized sheep erythrocytes. The results are shown in Table II.

As shown in Table II, it is clear that the extract of this invention increases the production of antihapten IgG (and IgM) antibody. Therefore, it is also clear that the extract of this invention possesses an immuno-activation effect and the production of antibodies other than allergic antibody is not reduced although it may be accelerated.

E. Antigenic cross reactivity:

The antigenic cross reactivity was determined by a gel precipitation reaction (Ouchterloney method).

Figure 3:
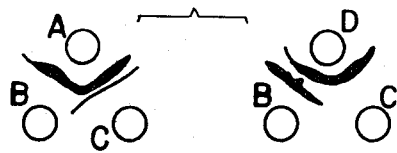
FIG. 3 shows cross reactive antigenicities by a gel precipitation (Ouchterloney method), and FIG. 4. is a graph showing the anticomplement effect of the extract of this invention.

Using rabbit anti-*Corynebacterium equi* anti serum and rabbit anti-tuberculin anti serum, a gel precipitation reaction was performed according to an method with the extract of this invention and PPD solution (TA$_2$) each adjusted to 10 mg/ml as antigens. The results are shown in FIG. 3. Ouchterloney FIG. 3 shows the fused precipitation lines of PPD solution (B) and the extract of this invention (C) against anti-*Corynebacterium equi* rabbit anti serum (A) in the left section and also the cross reactive antigenicity to the PPD solution (B) and to the extract of this invention (C) by the rabbit anti-tuberculin anti serum (D) in the right section.

From the results in FIG. 3, it is clear that the extract of this invention possesses an antigenic cross reactivity with PPD. Thus, the extract of this invention can be applied to tuberculin therapy in a more stable form.

F. Anticomplement effect:

After reacting the sera of SD rats with the extract of this invention at various concentrations for 1 hour at 37° C., the residual haemolytic activity of complement was measured using sheep erythrocytes sensitized by anti-SRBC antibody. The results are shown in FIG. 4.

Figure 4:
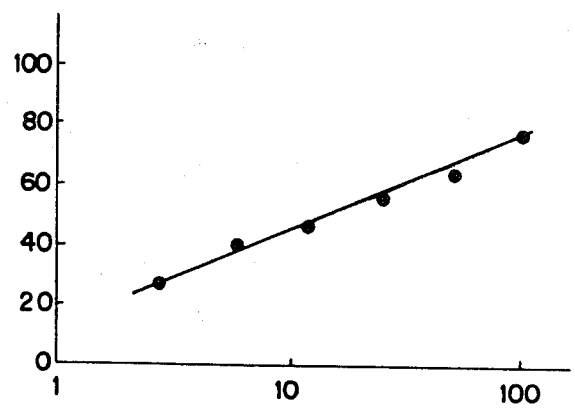

As it is clear from FIG. 4, it was confirmed by the inhibitory ratio in a haemolytic reaction of sheep erythrocytes that the extract of this invention had a remarkable anticomplement effect. Therefore, it is considered that the extract of this invention suppresses non-specific allergic reaction.

FIG. 4 shows the anticomplement effect of the extracts of this invention. The abscissa axis shows the addition amount ($\mu$g) of the extract of this invention and the ordinate axis shows the inhibitory ratio (%) of haemolytic reaction.

TABLE II

| | Increase of number of antihapten IgG, (IgM) antibody forming cell | | | | | | |
|---|---|---|---|---|---|---|---|
| | No. of tested mouse | 1 | 2 | 3 | 4 | 5 | Mean Value (± standard deviation) |
| The water soluble extract of this invention | Number of haemolytic plaques in an observation field | 240.3 | 229.5 | 230.5 | 117.0 | 119.0 | 187.8 ± 63.9 |
| | Number of haemolytic plaques $10^6$ nucleated spleen cells | 147.8 | 141.2 | 141.9 | 72.0 | 73.0 | 115.5 ± 39.4 |
| | Total number of haemolytic plaques per mouse | 6847 | 7738 | 7180 | 3240 | 3862 | 5773 ± 2065.4 |
| Primarily cultured broth (bacterial cells) | Number of haemolytic plaques in an observation field | 212.5 | 192.5 | 208.0 | 209.0 | 202.0 | 204.8 ± 7.9 |
| | Number of haemolytic plaques $10^6$ nucleated spleen cells | 130.8 | 118.5 | 134.8 | 130.5 | 120.0 | 126.9 ± 7.2 |
| | Total number of haemolytic plaques per mouse | 6344 | 7110 | 7144 | 7021 | 6318 | 6818 ± 329.3 |
| Control (normal saline solution) | Number of haemolytic plaques in an observation field | 17.0 | 45.5 | 16.5 | 18.0 | 46.5 | 28.7 ± 15.8 |
| | Number of haemolytic plaques $10^6$ nucleated spleen cells | 10.5 | 28.0 | 10.2 | 11.1 | 28.6 | 17.7 ± 9.7 |
| | Total number of haemolytic plaques per mouse | 430 | 1344 | 498 | 475 | 1224 | 794 ± 449.9 |

G. Toxicity:

The acute toxicity in the case of intraperitoneally administering the extract of this invention and the primary cultured broth (bacterial cells) thereof is as follows. In addition, since the primary cultured broth (bacterial cells) is insoluble in water, it was administered as an aqueous suspension.

Extract of the invention $LD_{50} > 20$ mg/mouse
Primary cultured broth (bacterial cells) $LD_{50}$ 5 mg/mouse From the above-described experimental results, it is clear that the extract of this invention shows very low toxicity as compared with the primary cultured broth (bacterial cells) for the extract.

In addition, in the tests of the effect on peripheral leukocyte counts and the effect on body weight gain in mice by the general test methods of "Minimum Requirement of Biological Products" (1973); Minist. of Health and Welfare, Japan.—3 General Testing Method—the extract of this invention shows no abnormality.

PRESCRIPTION EXAMPLE

An aqueous solution of 5 mg/ml of the extract (lyophilized product) of this invention was prepared, diluted 100 times the volume of the aqueous solution with isotonic sodium chloride solution, and 1 ml each of the diluted solution was filled in an ampule.

In the dosage of the injection of this invention, it is ordinarily administered by subcutaneous injection according to an ordinary desensitizing therapy in an amount of 0.1–0.8 ml per injection at an interval of 1-2 times per week.

What is claimed is:

1. A water soluble extract from *corynebacterium equi* Ko-85 Strain, the water soluble extract having a weight of protein content calculated as Bovine Serum Albumin to sugar content calculated as glucose of from 7.50:1 to 13.42:1, the ratio of the optical density at 260 nm to that at 280 nm from 1.56 to 1.62, an isoelectric point of 3.75–3.80, and having a suppressive effect on immunoglobulin E (IgE) antibody.

2. A water soluble extract from nonpathogenic aerobic corynebacteria produced by subjecting a cultured broth obtained by aerobically cultivating *corynebacterium equi* Ko-85 at a low temperature, grinding and homogenizing the cultured broth, subjecting the resulting homogenate to an ultrasonic treatment, adjusting the pH of an aqueous solution of the effective component thus obtained to 3.7–3.75 to form a precipitate, dialyzing the precipitate in a substantially neutral aqueous solution thereof, and lyophilizing the dialyzed product.

3. The product of claim 1, wherein the water soluble extract is a lyophilized product.

4. A pharmaceutical composition comprising an effective amount of the water soluble extract of claim 1 in combination with a pharmaceutically acceptable carrier.

* * * * *